(12) United States Patent
Purcell (10) Patent No.: US 7,776,608 B2
(45) Date of Patent: Aug. 17, 2010

(54) VOLUME METER TESTING DEVICE AND METHOD OF USE

(75) Inventor: D. Glenn Purcell, Edwardsburg, MI (US)

(73) Assignee: Bayer HealthCare LLC, Tarrytown, NY (US)

( * ) Notice: Subject to any disclaimer, the term of this patent is extended or adjusted under 35 U.S.C. 154(b) by 648 days.

(21) Appl. No.: 10/174,833

(22) Filed: Jun. 20, 2002

(65) Prior Publication Data

US 2003/0007893 A1 Jan. 9, 2003

Related U.S. Application Data

(60) Provisional application No. 60/303,550, filed on Jul. 9, 2001.

(51) Int. Cl.
*G01N 33/48* (2006.01)

(52) U.S. Cl. .................. 436/164; 436/169; 422/58; 422/61

(58) Field of Classification Search .......... 422/99, 422/102–104, 58, 61; 436/180, 164–166, 436/169
See application file for complete search history.

(56) References Cited

U.S. PATENT DOCUMENTS

| | | | |
|---|---|---|---|
| 4,088,448 A | 5/1978 | Lilja et al. | |
| 4,426,451 A | 1/1984 | Columbus | |
| 4,761,381 A * | 8/1988 | Blatt et al. | 436/165 |
| 4,876,067 A | 10/1989 | Deneke et al. | 422/56 |
| 4,935,346 A | 6/1990 | Phillips et al. | |
| 5,004,923 A | 4/1991 | Hilman et al. | |
| 5,039,617 A | 8/1991 | McDonald et al. | |
| 5,049,487 A | 9/1991 | Phillips et al. | |
| 5,286,454 A | 2/1994 | Nilsson et al. | |
| 5,304,468 A | 4/1994 | Phillips et al. | |
| 5,472,671 A * | 12/1995 | Nilsson et al. | 422/102 |
| 5,520,883 A | 5/1996 | Charlton et al. | 422/56 |
| 5,611,999 A | 3/1997 | Dosmann et al. | 422/82.05 |
| 5,679,311 A | 10/1997 | Harttig et al. | |
| 5,681,484 A | 10/1997 | Zanzucchi et al. | |
| 5,700,695 A | 12/1997 | Yassinzadeh et al. | |
| 5,723,284 A | 3/1998 | Ye | 435/4 |
| 5,759,364 A | 6/1998 | Charlton et al. | |
| 5,770,389 A | 6/1998 | Ching et al. | |
| 5,814,522 A | 9/1998 | Zimmer et al. | 436/170 |
| 5,843,691 A | 12/1998 | Douglas et al. | |
| 5,962,215 A | 10/1999 | Douglas et al. | |
| 6,036,919 A | 3/2000 | Thym et al. | |

(Continued)

FOREIGN PATENT DOCUMENTS

EP 0 269 240 A1 6/1988

(Continued)

*Primary Examiner*—Lyle A Alexander
(74) *Attorney, Agent, or Firm*—Nixon Peabody LLP (57) ABSTRACT

A test device adapted to test a concentration of an analyte in a fluid has a pickup area having a first volume for receiving the fluid. In fluid communication with the pickup area is a read area having a second volume, which is less than the first volume. Since the second volume is less than the first volume, fluid from the pickup area will flow into the read area only after the pickup area is full. The read area also contains a reagent that is adapted to indicate the concentration of the analyte in the fluid.

38 Claims, 6 Drawing Sheets

U.S. PATENT DOCUMENTS

| | | | |
|---|---|---|---|
| 6,156,270 A * | 12/2000 | Buechler | 422/58 |
| 6,206,841 B1 | 3/2001 | Cunningham et al. | |
| 6,207,000 B1 | 3/2001 | Schwobel et al. | |
| 6,300,138 B1 * | 10/2001 | Gleason et al. | 436/165 |
| 6,368,563 B1 * | 4/2002 | Allen et al. | 422/102 |
| 6,403,037 B1 * | 6/2002 | Chang et al. | 422/68.1 |
| 6,531,322 B1 | 3/2003 | Jurik et al. | |
| 6,818,180 B2 | 11/2004 | Douglas et al. | |
| 6,916,410 B2 | 7/2005 | Katsuki | |
| 6,949,297 B2 | 9/2005 | Yang et al. | |
| 6,986,869 B2 | 1/2006 | Tuohy et al. | |
| 7,008,799 B1 | 3/2006 | Zimmer et al. | |
| 2002/0009387 A1 | 1/2002 | Hirayama | |
| 2002/0168290 A1 | 11/2002 | Yuzhakov et al. | |
| 2003/0007893 A1 | 1/2003 | Purcell | |
| 2003/0013147 A1 | 1/2003 | Hildenbrand | |
| 2003/0059948 A1 | 3/2003 | Hildenbrand et al. | |
| 2003/0171696 A1 | 9/2003 | Dosmann | |
| 2004/0028558 A1 | 2/2004 | Pollock et al. | |
| 2004/0054267 A1 | 3/2004 | Feldman et al. | |
| 2004/0161365 A1 | 8/2004 | Siu Yu | |

FOREIGN PATENT DOCUMENTS

| | | |
|---|---|---|
| EP | 0 443 231 A1 | 2/1990 |
| EP | 0 483 117 A2 | 4/1992 |
| EP | 0 974 840 A2 | 1/2000 |
| EP | 1203823 | 5/2002 |
| EP | 1389443 | 2/2004 |
| JP | 08145980 | 6/1996 |
| JP | 09133673 | 5/1997 |
| WO | WO01/62385 | 8/2001 |
| WO | WO01/72220 | 10/2001 |
| WO | WO2005/077274 | 8/2005 |
| WO | WO2005/112742 | 12/2005 |
| WO | WO2006/065898 | 6/2006 |

* cited by examiner

VOLUME METER TESTING DEVICE AND METHOD OF USE

CROSS-REFERENCE TO RELATED APPLICATION

This application claims the benefit of the U.S. Provisional Application 60/303,550, filed on Jul. 9, 2001.

FIELD OF THE INVENTION

The present invention relates generally to blood monitoring devices and, more particularly, to a volume metering test device for obtaining a sample of blood.

BACKGROUND OF THE INVENTION

It is often necessary to quickly obtain a sample of blood and perform an analysis of the blood sample. One example of a need for quickly obtaining a sample of blood is in connection with a blood glucose monitoring system where a user must frequently use the system to monitor the user's blood glucose level.

Those who have irregular blood glucose concentration levels are medically required to self-monitor their blood glucose concentration level. An irregular blood glucose level can be brought on by a variety of reasons including illness, such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low, a condition known as hypoglycemia, a person can become nervous, shaky, and confused. That person's judgment may become impaired and that person may eventually pass out. A person can also become very ill if their blood glucose level becomes too high, a condition known as hyperglycemia. Both conditions, hypoglycemia and hyperglycemia, are potentially life-threatening emergencies.

Figure 1:
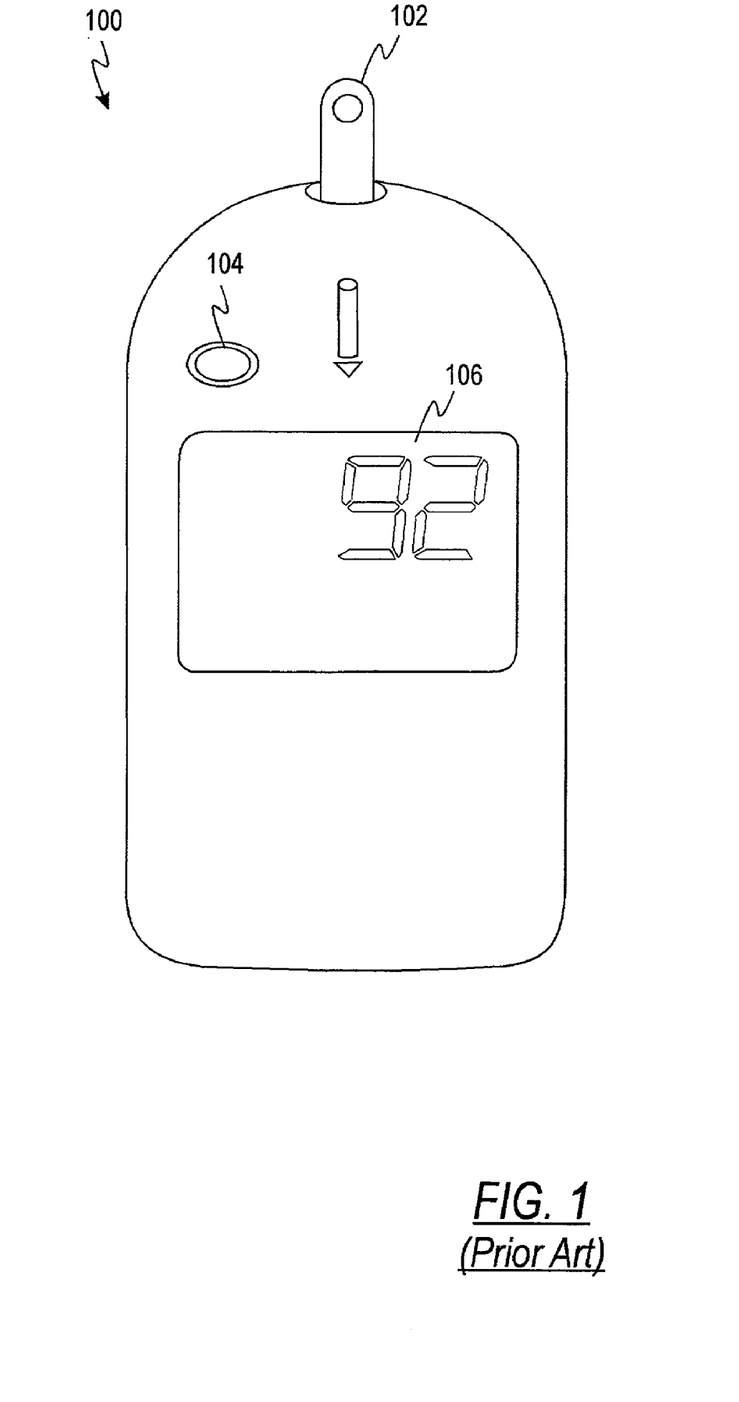
FIG. 1 is a top view of a prior art blood glucose testing device.
Figure 2:
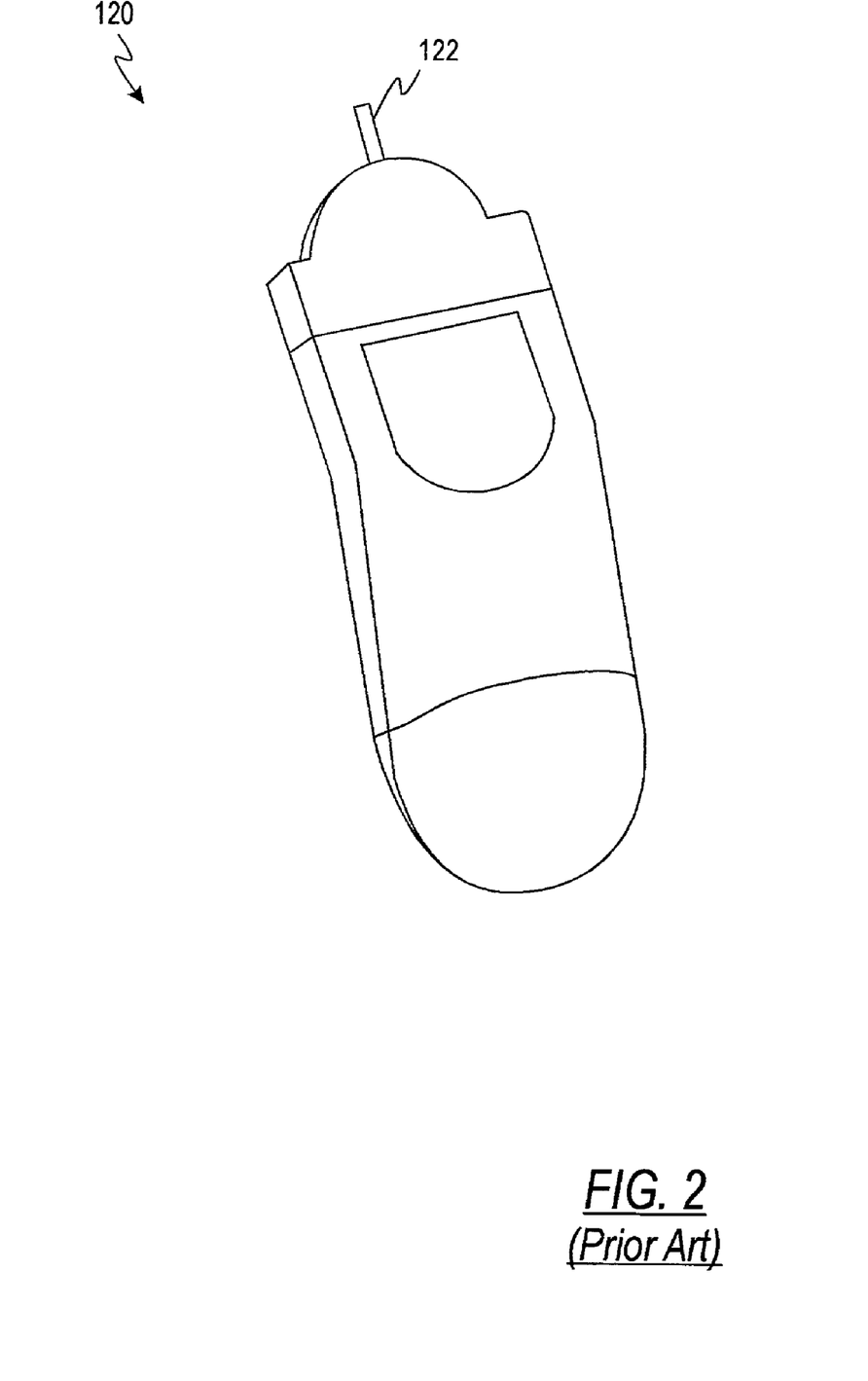
FIG. 2 is a perspective view of a prior art lance.

One method of monitoring a person's blood glucose level is with a portable, hand-held blood glucose testing device. A prior art blood glucose testing device 100 is illustrated in FIG. 1. The portable nature of these devices 100 enables the users to conveniently test their blood glucose levels wherever the user may be. The glucose testing device contains a test sensor 102 to harvest the blood for analysis. The device 100 contains a switch 104 to activate the device 100 and a display 106 to display the blood glucose analysis results. In order to check the blood glucose level, a drop of blood is obtained from the fingertip using a lancing device. A prior art lancing device 120 is illustrated in FIG. 2. The lancing device 120 contains a needle lance 122 to puncture the skin. Some lancing devices implement a vacuum to facilitate drawing blood. Once the requisite amount of blood is produced on the fingertip, the blood is harvested using the test sensor 102. The test sensor 102, which is inserted into a testing unit 100, is brought into contact with the blood drop. The test sensor 102 draws the blood to the inside of the test unit 100, which then determines the concentration of glucose in the blood. Once the results of the test are displayed on the display 106 of the test unit 100, the test sensor 102 is discarded. Each new test requires a new test sensor 102.

One problem associated with some conventional test sensors is that the proper amount of blood may not be obtained. The test sensor used needs a minimum amount of blood to provide accurate results. If the proper amount of blood is not received, inaccurate results may be generated.

Another problem associated with some conventional test sensors is that the user cannot ensure that the proper amount of blood has been obtained. The user applies the blood directly onto a read area and then obtains a reading from the device. If an unusual reading is given, the user may surmise that the unusual reading was caused by an improper amount of blood being obtained. The user may then try again. There is no way for the user to know, however, if that is the true reason for the unusual result.

Another problem associated with some conventional test sensors is the presence of air gaps in the blood sample that is being read. Air gaps in the blood sample can also cause inaccurate readings, requiring the user to retest.

Another problem associated with some conventional test sensors is that the user's blood physically contacts the elements within the testing unit. Cross-contamination can be a problem if the monitoring device is used by more than one user, such as in a doctor's office or other clinical setting.

SUMMARY OF THE INVENTION

A test sensor adapted to test a concentration of an analyte in a fluid has a pickup area having a first volume for receiving the fluid. In fluid communication with the pickup area is a read area having a second volume, which is less than the first volume. Since the second volume is less than the first volume, fluid from the pickup area will flow into the read area only after the pickup area is full. The read area also contains a reagent that is adapted to indicate the concentration of the analyte in the fluid.

BRIEF DESCRIPTION OF THE DRAWINGS

The foregoing and other advantages of the invention will become apparent upon reading the following detailed description and upon reference to the drawings.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DESCRIPTION OF ILLUSTRATIVE EMBODIMENTS

Figure 3:
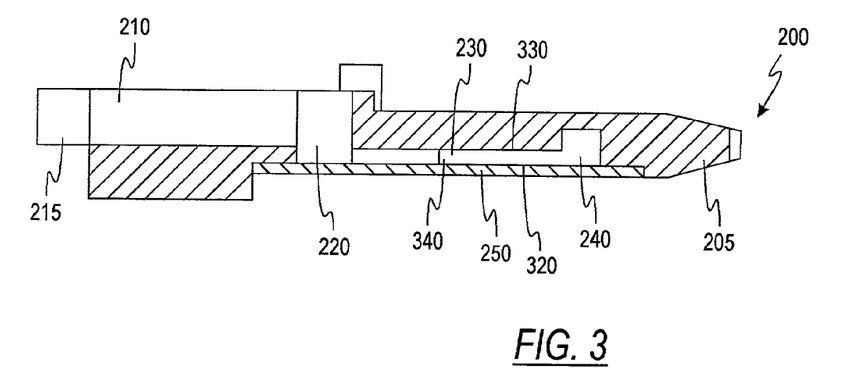
FIG. 3 is a side view of a test device according to one embodiment of the present invention.

FIG. 3 depicts a schematic view of the side of a test device 200 according to one embodiment of the present invention.

The test device 200 includes a format 205, a pickup area 210, a transfer area 220, a read area 230, a vent area 240, and a cover 250. The test device 200 is designed to collect a fluid, for example, blood, so the fluid may be tested for the concentration of a particular analyte, such as glucose. In describing the details of the operation of the test device 200, the fluid described will be blood pricked from a finger and the analyte will be glucose. It is understood that the embodiment may also be used for other fluids and analytes and that these only serve as examples.

After a finger is pricked for blood, the pickup area 210 is placed in contact with the wound. Using capillary action, described below, the blood moves into the pickup area 210. The blood flows from the pickup area into the transfer area 220 and then into the read area 230. The cover 250 develops the capillary gap in the read area 230 and also retains the blood within the test device, protecting the test unit from contamination.

The read area 230 includes a reagent which is designed to react with the glucose to produce a colormetric or electrochemical response. The test unit 100 then measures the colormetric or electrochemical response. The reagent used in the read area 230 depends on the type of analyte desired.

In one embodiment, the test device 200 can be used in conjunction with a photometric test unit, which measures the colormetric reaction. In photometric testing, the reagent used causes a change in color in the read area. The photometric test unit then reads the amount of color change. Photometric testing is described in more detail in commonly-owned U.S. Pat. No. 5,611,999 entitled "Diffuse Reflectance Readhead" which is incorporated herein by reference in its entirety. It is also contemplated that other methods of testing the concentration of glucose in blood may be utilized.

In another embodiment of the test device 200, an electrochemical test unit is employed. The read area 230 includes a pair of electrodes (not shown). In electrochemical analysis, the change in current across the electrodes caused by the reaction of the glucose and the reagent creates an oxidation current at the electrodes which is directly proportional to the user's blood glucose concentration. The current can be measured by an electrochemical test unit coupled to a pair of terminals (not shown) corresponding to the electrodes. The electrochemical test unit can then communicate to the user the blood glucose concentration. An example of an electrochemical test system is described in detail by commonly-owned U.S. Pat. No. 5,723,284 entitled "Control Solution And Method For Testing The Performance Of An Electrochemical Device For Determining The Concentration Of An Analyte In Blood" which is incorporated herein by reference in its entirety.

Figure 4:
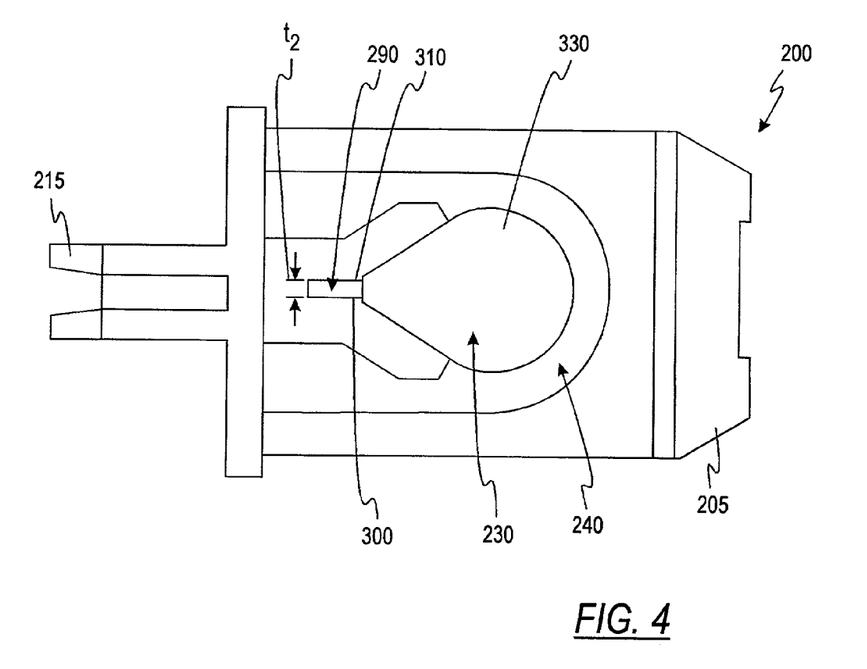
FIG. 4 is a bottom view of the test device illustrated in FIG. 3.
Figure 5:
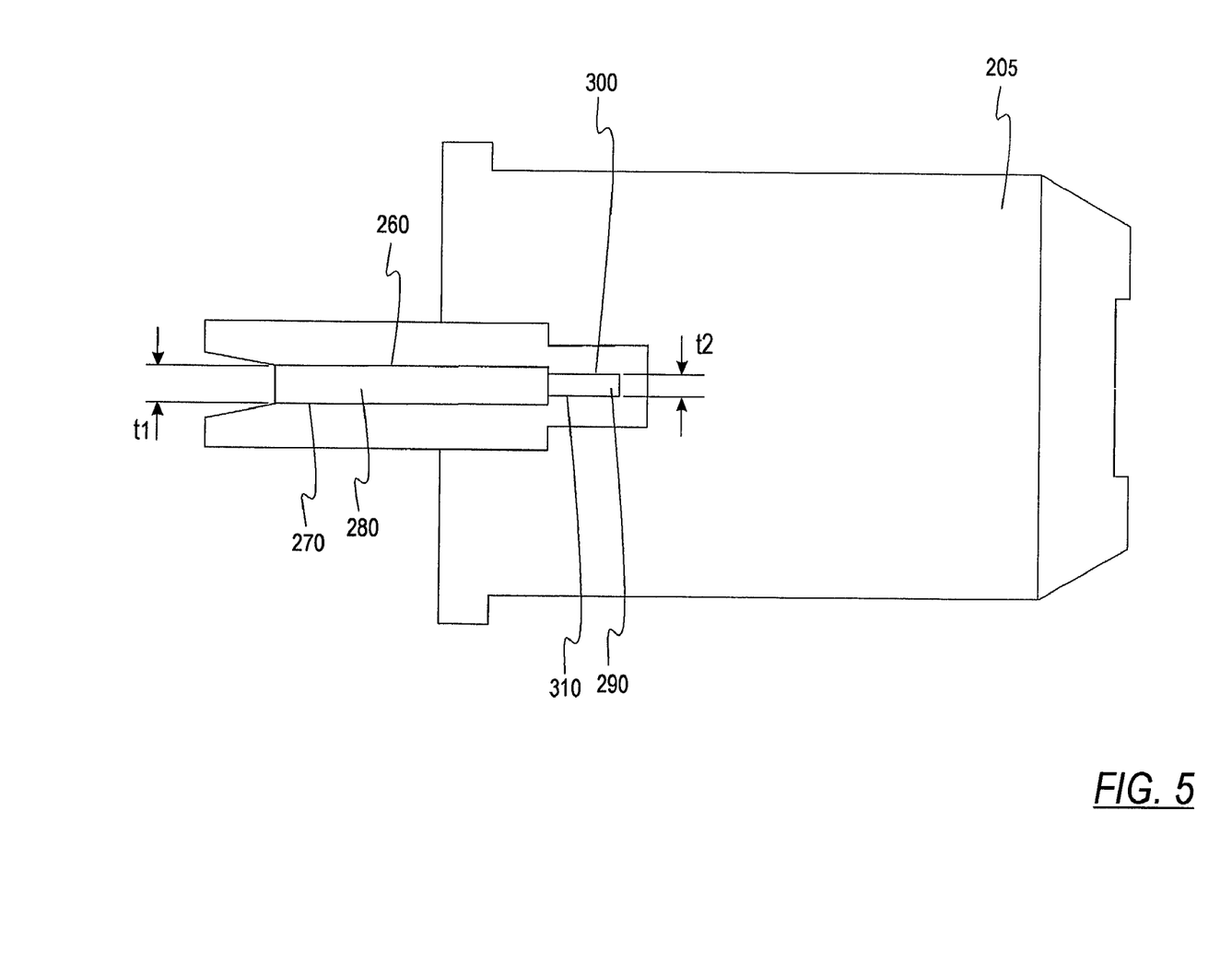
FIG. 5 is a top view of the test device illustrated in FIG. 3.

Referring now to FIGS. 3 through 5, a side view, a bottom view, and a top view are shown. Through capillary action, the blood flows into the test device 200 at the pickup area 210. The pickup area 210 has a first sidewall 260 and a second sidewall 270, which create a capillary gap 280 having a thickness $t_1$. The capillary gap 280, thus, facilitates the capillary action. Proceeding the pickup area 210 is a nib 215. The nib 215 does not have either a floor or a ceiling. Elimination of a floor and a ceiling at the pickup area 210 insures that the pickup area 210 is not closed when the nib 215 is in direct contact with the wound on the finger. Closing the pickup area 210 entirely could create a vacuum which potentially destroys the capillary action. The pickup area 210 has a volume $v_1$, which is larger than the required volume needed to accurately test the blood. The volume $v_1$ of the pickup area 210 is designed to ensure that at least a requisite amount of blood is obtained with each test. Creating a large pickup area 210 decreases the likelihood that a user will need to retest due to lack of a sufficient volume of blood.

The transfer area 220 is in fluid communication with the pickup area 210 and the read area 230. The transfer area 220 is designed to transfer the blood from the pickup area 210 to the read area 230. A second capillary gap 290 having a thickness of $t_2$ is created in the transfer area by a first and second sidewall 300, 310. The thickness $t_2$ of the second capillary gap 290 is less than the thickness of $t_1$ of the first capillary gap 280. The blood will not flow into an area with a smaller capillary gap until the area with the larger capillary gap is completely filled. In other words, an area with a smaller capillary gap cannot exert enough force to draw blood from an area having a larger capillary gap. Once the pickup area 210 is full of the blood, then the blood flows into the area with the smaller capillary gap. The transfer area 220 has a volume $v_2$ which is less than the volume $v_1$ of the pickup area 210. Since the volume $v_1$ of the pickup area 210 is larger than the volume $v_2$ of the transfer area and the pickup area 210 must be filled prior to the transfer area 220 drawing the blood, the testing device 200 ensures that at least a requisite amount of blood is obtained from the user.

After filling the transfer area 220 with blood, the blood next flows into the read area 230 by way of capillary action. The read area 230 is an island surrounded by the vent area 240. As blood moves into the read area 230, the air in the read area 230 escapes into the vent area 240. This ensures that the blood continues to flow into the read area 230 and also aids in the prevention of air pockets forming in the read area 230 during the testing process. The read area 230 comprises a floor 320 and a ceiling 330. The floor 320 is a top side of the cover 250. The ceiling 330 is a portion of the format, illustrated in FIG. 3. The read area 230 does not include any sidewalls. The inventor has found that air can become trapped along the sidewalls of the read area 230. The presence of air in the read area 230 increases the risk of obtaining an inaccurate result. By eliminating the sidewalls, air cannot become entrapped in the read area 230, as it all flows out into the vent area 240, and the possibility of erroneous test results is decreased.

Figure 6:
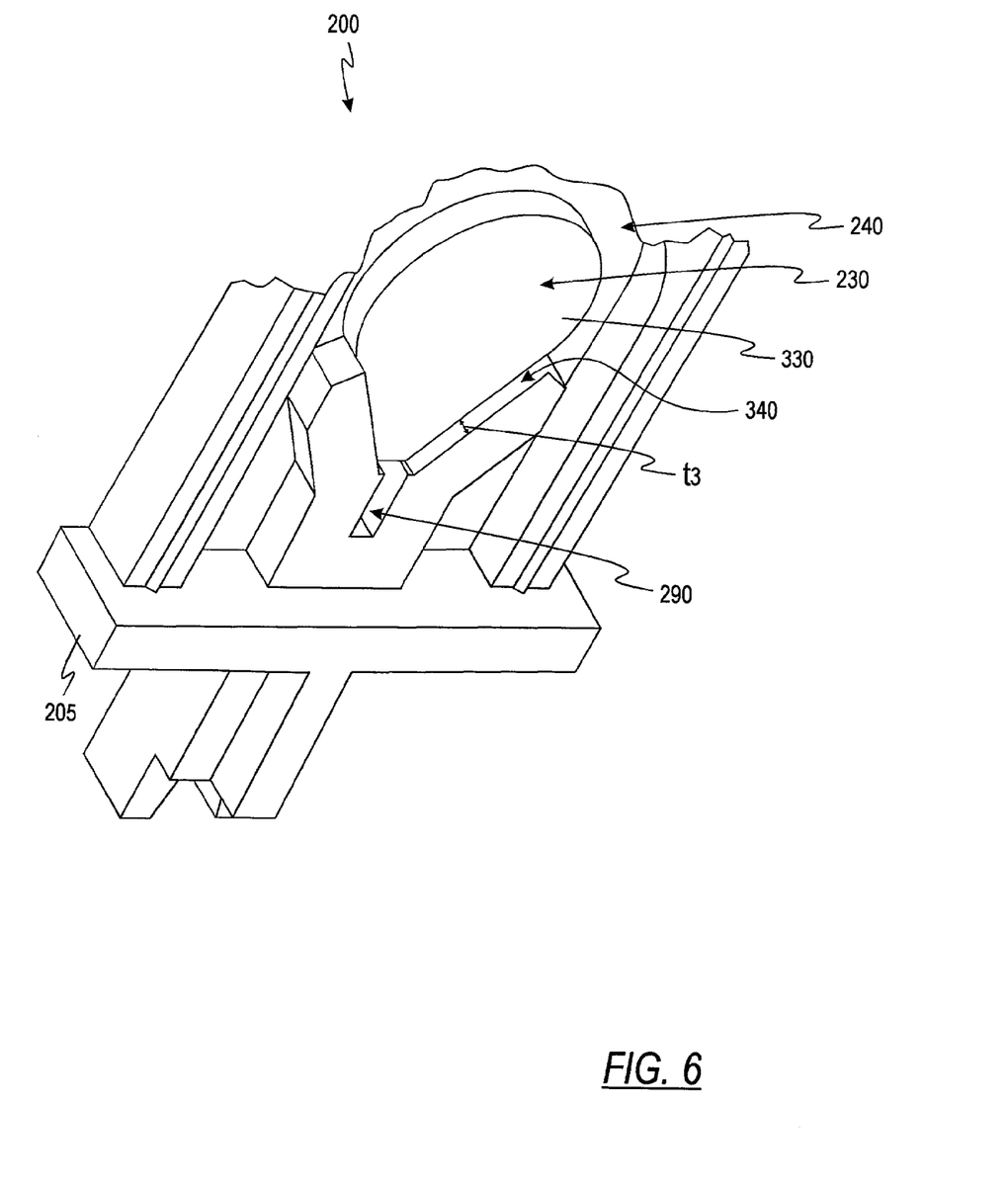
FIG. 6 is a perspective view of the test device illustrated in FIG. 3, with a portion removed to better illustrate a read portion of the test device.

To ensure a complete filling of the read area 230, the floor 320 and ceiling 330 create a capillary gap 340 having a thickness $t_3$ (FIG. 6) that is less than the thickness $t_2$ of the capillary gap 290 of the transfer area 220. Therefore, blood will not move into the read area 230 until the transfer area 220 is completely filled. The read area 230 has a volume $v_3$ which is less than the volume $v_2$ of the transfer area. Thus, once the transfer area 220 is completely filled, there is enough blood drawn into the testing device 200 to insure a proper reading. Since the read area 230 will not begin to draw the blood from the transfer area 220 until the transfer area 220 is full, a user may be assured that enough blood to provide an accurate reading has been obtained. The capillary gap 340 is maintained at a thickness $t_3$ because the format 205 (the ceiling 330) is made of a plastic film that retains its shape.

In one embodiment, the volume $v_3$ of the read area is from about 70 to about 80 percent of the volume $v_1$ of the pickup area. In another embodiment, the pickup area 210 has a volume of from about 5.0 to about 5.5 microliters and the read area 230 has a volume from about 3.5 to about 4.0 microliters. The volume $v_2$ of the transfer area 220 may be anywhere between the volume $v_1$ of the pickup area 210 and the volume $v_3$ of the read area 230.

In one embodiment, the thickness $t_1$ of the first capillary gap 280 is in the range of about 0.025 to about 0.030 inch. The thickness $t_2$ of the second capillary gap 290 is in the range of about 0.015 to about 0.020 inch. The thickness $t_2$ of the second capillary gap 290, however, is less than the thickness $t_1$ of the first capillary gap 280. The thickness $t_3$ of the third capillary gap 340 is in the range of about 0.008 to about 0.0012 inch. The thickness $t_3$ of the third capillary gap 340 must remain less than the thicknesses $t_1$ and $t_2$ of the first and second capillary gaps 280, 290.

The operation of the device will now be described. The user moves the pickup area 210 into contact with a drop of blood on the user's fingertip. The pickup area 210 then fills with blood from the user's fingertip. Once the pickup area 210 is fill, the transfer area 220 begins to fill with the blood. As discussed above, once the transfer area 220 begins to fill with blood, the user may then remove the testing device 200 from the user's fingertip. Since the transfer area 220 does not begin to fill with blood until after the pickup area is filled, and the pickup area has a volume $v_1$ greater than the requisite volume needed for an accurate reading, the user can be assured that enough blood has been drawn.

Once the blood has filled the transfer area 220, the blood then begins to fill the read area 230. After the read area 230 is filled with blood, the sensor then reads the resulting change and indicates the glucose concentration to the user.

Figure 7:
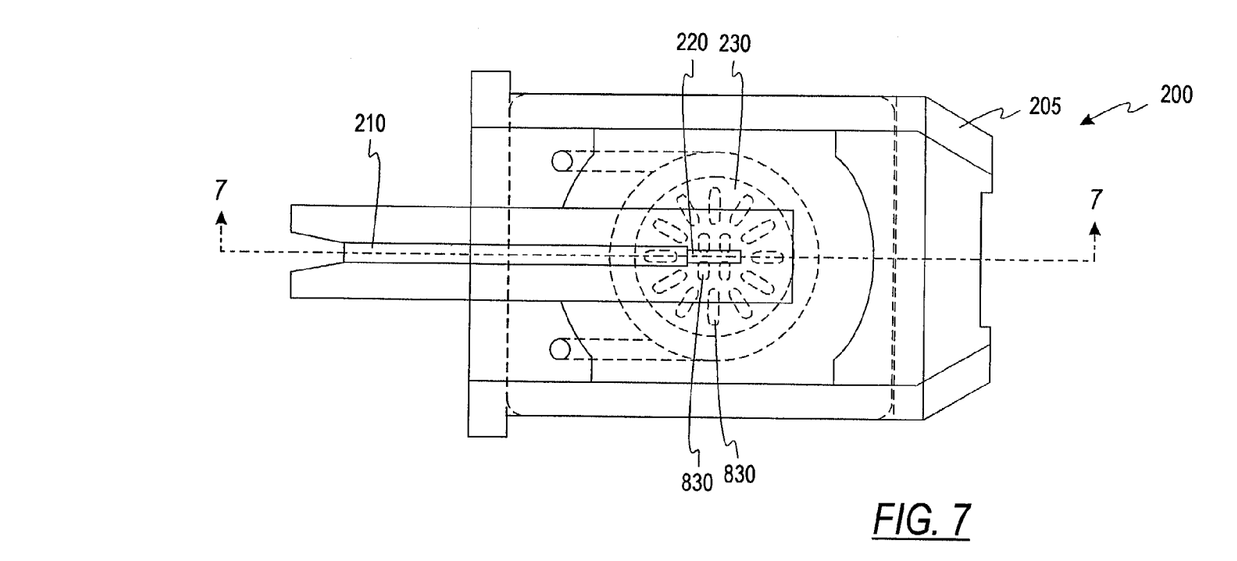
FIG. 7 is a top view of another embodiment of the test device.
Figure 8:
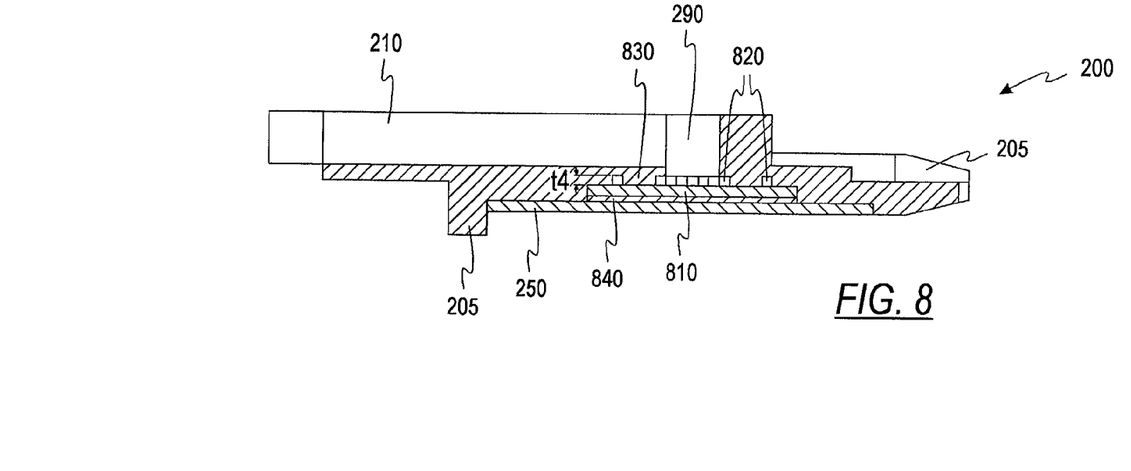
FIG. 8 is a side view of the test device illustrated in FIG. 7, cut along line B-B.

Turning now to FIGS. 7 and 8, an alternate embodiment of the test device 200 will be described. FIG. 7 is a top view of the test device, and FIG. 8 is a perspective view of the test device of FIG. 7, cut along line 7-7. Features that are the same as the previous embodiment will be numbered the same in this embodiment. In this embodiment, the read area 230 includes a capillary gap 820 created by supports 830, a filter 810, and a reagent impregnated paper 840. The filter 830 and reagent impregnated paper 840 are below the capillary gap 820. In this configuration, the blood needs to pass through the filter 810 before the reagent reacts with the blood. It is also important to have the blood sample spread uniformly across the surface of the filter 810 prior to penetrating the filter 810 and reaching the top surface of the reagent impregnated paper 840, penetrating the reagent impregnated paper 840 and reacting with the reagent.

The capillary gap 820 above the filter 810 is produced by supports in the test device 200 and is arranged in such a pattern to promote spreading across the top surface of the filter 810. Thus, a uniform color change can be created along the read surface of the reagent impregnated paper 840, allowing for an accurate reading by a photometric test unit.

The capillary gap distance $t_4$ is less than the thickness $t_2$ of the capillary gap 290 of the transfer area 220. Thus, the flow of blood acts the same in this embodiment.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the claimed invention, which is set forth in the following claims.

What is claimed is:

1. A test device adapted to test a concentration of an analyte in a fluid comprising:
    a pickup area having a first volume for receiving the fluid; and
    a contiguous cover having a read area, a floor of the read area being a top side of the cover, the read area being in fluid communication with the pickup area, the read area including an island having a gap, the read area further including a vent area adjacent to and surrounding the island, the read area being adapted to receive fluid from the pickup area only after the pickup area is full, the read area containing a reagent adapted to produce a reaction indicative of the concentration of the analyte in the fluid, a thickness of the vent area being greater than a thickness of the gap of the island.

2. The test device according to claim 1, wherein the pickup area comprises a first sidewall and a second sidewall independent of a floor or a ceiling.

3. The test device according to claim 1, wherein the read area further comprises a ceiling.

4. The test device according to claim 3, wherein the ceiling of the read area is a plastic film.

5. The test device according to claim 3, wherein the ceiling of the read area is a porous paper.

6. The test device according to claim 5, wherein the floor of the read area is a filter.

7. The test device according to claim 5, wherein the ceiling of the read area includes at least one support, adapted to hold the ceiling a predetermined distance from the floor.

8. The test device according to claim 1, further comprising a transfer area in fluid communication with the read area and the pickup area, adapted to transfer the fluid from the pickup area into the read area.

9. The test device according to claim 8, wherein the transfer area has a volume which is less than the first volume of the pickup area and larger than a volume of the read area.

10. The test device according to claim 9, wherein the transfer area has sidewalls which are thinner than a sidewall of the pickup area.

11. The test device according to claim 8, wherein each of the pickup area, and the transfer area has gaps to draw the fluid into the pickup area and the transfer area.

12. The test device according to claim 11, wherein the gap of the pickup area is thicker than the gap of the transfer area.

13. The test device according to claim 11, wherein the gap of the transfer area is thicker than the gap of the read area.

14. The test device according to claim 1, wherein a volume of the read area is in the range of about 70 to about 80 percent as large as the first volume.

15. The test device according to claim 14, wherein the volume of the read area is in the range of about 3.5 to about 4.0 microliters and the first volume is in the range of about 4.5 to about 5.5 microliters.

16. The test device according to claim 1, wherein the reagent is adapted to produce a colorimetric reaction.

17. The test device according to claim 16, in combination with a colorimetric sensor.

18. The test device according to claim 1, wherein the reagent is adapted to produce an electrochemical reaction.

19. The test device according to claim 18, in combination with an electrochemical sensor.

20. A test device adapted to test a concentration of an analyte in a fluid, comprising:
    a pickup area having a first gap adapted to use capillary action to draw the fluid into the pickup area; and
    a contiguous cover having a read area, a bottom of the read area being a top side of the cover, the read area being in fluid communication with the pickup area, the read area including an island and a vent area adjacent to and surrounding the island, the island having a second gap such that the fluid is drawn into the second gap of the read area only after the first gap of the pickup area is entirely filled, the read area containing a reagent adapted to produce a reaction indicative of the concentration of the analyte in the fluid, a thickness of the vent area being greater than a thickness of the second gap of the island.

21. The test device according to claim 20, wherein the pickup area comprises a first sidewall and a second sidewall independent of a floor or a ceiling.

22. The test device according to claim 20, wherein the pickup area has a first volume and the read area has a second volume, such that the first volume of the pickup area is greater than the second volume of the read area.

23. The test device according to claim 22, wherein the second volume of the read area is from about 70 to about 80 percent as large as the first volume of the pickup area.

24. The test device according to claim 22, wherein the second volume of the read area is from about 3.5 to about 4.0 microliters and the first volume of the pickup area is from about 4.5 to about 5.5 microliters.

25. The test device according to claim 20, further comprising a transfer area in fluid communication with the read area and the pickup area, adapted to transfer the analyte from the pickup area into the read area.

26. The test device according to claim 25, wherein the pickup area has a first volume, the read area has a second volume, and a transfer area has a third volume, the third volume being less than the first volume of the pickup area and larger than the second volume of the read area.

27. The test device according to claim 20, wherein the second gap of the island comprises a top and a bottom independent of any sidewalls.

28. The test device according to claim 27, wherein the bottom of the read area is a porous paper.

29. The test device according to claim 28, wherein a top of the read area is a filter.

30. The test device according to claim 29, wherein the top of the read area includes at least one support, adapted to hold the top a predetermined distance from the bottom.

31. The test device according to claim 20, wherein the reagent is adapted to produce a colorimetric reaction.

32. The test device according to claim 31, in combination with a colorimetric sensor.

33. The test device according to claim 20, wherein the reagent is adapted to produce an electrochemical reaction.

34. The test device according to claim 33, in combination with an electrochemical sensor.

35. A test device adapted to test a concentration of an analyte in a fluid, comprising:
   a pickup area having a first volume for receiving the fluid and a first gap adapted to use capillary action to draw the fluid into the pickup area; and
   a contiguous cover having a read area, a bottom of the read area being a top side of the cover, the read area being in fluid communication with the pickup area, the read area including an island and a vent area adjacent to and surrounding the island, the island having a second gap such that the fluid is drawn into the second gap after the first gap is entirely filled, the read area containing a reagent adapted to produce a reaction indicative of the concentration of the analyte in the fluid, wherein a thickness of the vent area is greater than a thickness of the second gap.

36. A test device adapted to test a concentration of an analyte in a fluid comprising:
   a pickup area having a first volume for receiving the fluid; and
   a contiguous cover having a read area, a bottom of the read area being a top side of the cover, the read area being in fluid communication with the pickup area, the read area configured to receive fluid from the pickup area only after the pickup area is full, the read area including a reagent adapted to produce a reaction indicative of the concentration of the analyte in the fluid, the read area further including an island, a capillary gap, and a vent area adjacent to and surrounding the island, the vent area being in fluid communication with the capillary gap, a thickness of the vent area being greater than a thickness of the capillary gap of the island.

37. A method for determining a concentration of an analyte in a fluid with a test device, the test device comprising a pickup area and a contiguous cover having a read area, a bottom of the read area being a top side of the cover, the read area including an island and a capillary gap, the read area including a reagent and being adjacent to and surrounded by a vent area and being in fluid communication with the pickup area, the method comprising the acts of:
   drawing the fluid into the pickup area, the pickup area having a first volume;
   filling the pickup area with the fluid;
   drawing the fluid into the read area after the pickup area is substantially full of the fluid, the read area having a second volume; and
   allowing air to escape into the vent area, the vent area being in fluid communication with the capillary gap, a thickness of the vent area being greater than a thickness of the capillary gap of the island.

38. The test device according to claim 1, wherein the gap of the island comprises a top and a bottom independent of any sidewalls.

* * * * *

UNITED STATES PATENT AND TRADEMARK OFFICE
CERTIFICATE OF CORRECTION

| | | |
|---|---|---|
| PATENT NO. | : 7,776,608 B2 | Page 1 of 1 |
| APPLICATION NO. | : 10/174833 | |
| DATED | : August 17, 2010 | |
| INVENTOR(S) | : D. Glenn Purcell | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 744 days.

Signed and Sealed this
Eighth Day of February, 2011

David J. Kappos
*Director of the United States Patent and Trademark Office*